United States Patent [19]

Nakamura et al.

[11] 4,351,964

[45] Sep. 28, 1982

[54] PROCESS FOR PRODUCING ACETALDEHYDE

[75] Inventors: Seishiro Nakamura; Masuhiko Tamura, both of Kurashiki, Japan

[73] Assignee: Kuraray Co., Ltd., Kurashiki, Japan

[21] Appl. No.: 261,805

[22] Filed: May 8, 1981

[30] Foreign Application Priority Data

May 19, 1980 [JP] Japan ................................. 55-66831
May 19, 1980 [JP] Japan ................................. 55-66832
Mar. 9, 1981 [JP] Japan ................................. 56-34269

[51] Int. Cl.$^3$ ....................... C07C 47/06; C07C 45/41
[52] U.S. Cl. ...................................... 568/484; 568/489
[58] Field of Search .............................. 568/484, 489

[56] References Cited

U.S. PATENT DOCUMENTS 3,579,566  5/1971  Fenton ................................. 568/484
3,631,188  12/1971  Wakamatsu et al. ............... 568/484

OTHER PUBLICATIONS

Musso et al., "Chemische Berichte" vol. 95 NR 5-8 (1962).

*Primary Examiner*—Werren B. Lone
*Attorney, Agent, or Firm*—Burns, Doane, Swecker & Mathis

[57] ABSTRACT

A process for producing acetaldehyde is disclosed, which comprises reacting acetic anhydride with hydrogen in gaseous phase in the presence of a supported catalyst comprising a palladium, a platinum or a rhodium component.

2 Claims, No Drawings

PROCESS FOR PRODUCING ACETALDEHYDE

This invention relates to a process for producing acetaldehyde by reaction of acetic anhydride with hydrogen.

An industrial process for producing acetaldehyde primarily uses ethylene as starting material, but because of the possiblity of future depletion of oil resources, researchers are getting more interested in the development of a process that uses a starting material other than ethylene. One example of such process is to react acetic anhydride with hydrogen. Several methods that rely on this technique have been proposed and they include (1) reacting acetic anhydride with hydrogen in liquid phase at room temperature and under atmospheric pressure in the presence of a platinum oxide or a palladium catalyst supported on barium sulfate (Chem. Ber., 95, 1844 (1962), (2) producing acetaldehyde from acetic anhydride and synthesis gas in the presence of a cobalt carbonyl catalyst (U.S. Pat. No. 3,631,188), and (3) producing acetaldehyde by reacting acetic anhydride with hydrogen in liquid phase at 100°–200° C. under pressure in the presence of rhodium chloride and triphenylphosphine (U.S. Pat. No. 3,579,566). However, these methods that use acetic anhydride as starting material have the following problems that must be solved before the methods can be used on an industrial scale. The problems of the method (1) are that acetaldehyde is produced in a small amount, that a considerable amount of ethyl alcohol is produced as a by-product, and that the catalyst component is partially dissolved in the reaction mixture and the catalytic activity is lost in a short period of time. The defects of the method (2) are that high temperature and high pressure are required to produce acetaldehyde in high yield and that a large amount of ethylidene diacetate is formed as a by-product. The method (3) is also not advantageous because a large amount of ethylidene diacetate (i.e. about twice that of acetaldehyde) is formed as a by-product, with the result that the selectivity for acetaldehyde significantly decreases.

It has now been found that the above-mentioned problems can be solved by reacting acetic anhydride with hydrogen in gaseous phase in the presence of a catalyst selected from the group consisting of a supported palladium catalyst, a supported platinum catalyst and a supported rhodium catalyst. According to this invention the formation of by-products is minimized and acetaldehyde is produced in high yield and high selectivity. In addition, the process of this invention leads to the possibility of carrying out the reaction under relatively low pressure.

Moreover, it has been found that when acetic acid is contained in a gaseous mixture to be supplied to the reaction in an amount of at least 3 mol%, based on the amount of acetic anhydride, the catalytic activity can be kept stable over a prolonged period of time with the yield and the selectivity being maintained at a high level. The amount of acetic acid to be contained in the gaseous mixture is, as afore-mentioned, at least 3 mol%, preferably 10 to 100 mol%, based on the amount of acetic anhydride. If the amount of acetic acid is less than 3 mol%, based on the amount of acetic anhydride, no substantial effect of acetic acid on catalyst life can be obtained. Although there is no critical upper limit to the amount of acetic acid, it is preferable in respect of the rate of reaction that the amount is not more than 200 mol%, based on the amount of acetic anhydride. The procedure for adding acetic acid to the gaseous mixture may be any of, for example,: (1) the procedure comprising vaporizing acetic acid and acetic anhydride separately and mixing the vapors; or (2) the procedure comprising mixing acetic acid and acetic anhydride and vaporizing the mixture in an evaporator.

In the process of this invention, acetic acid is produced in addition to acetaldehyde. Acetaldehyde and acetic acid are usually produced in about equal proportion although the proportion slightly varies with temperature and other reaction conditions.

The catalyst for use in the practice of this invention is selected from the group consisting of a supported palladium catalyst, a supported platinum catalyst and a supported rhodium catalyst. Among these, a supported palladium catalyst is most preferred in view of catalytic activity and selectivity. Carriers that can be used to support palladium, platinum or rhodium include, for example, alumina, silica, silica-alumina, titania, zirconia and activated carbon. The concentration of palladium, platinum or rhodium based on the carrier is not critical, but it is generally in the range of from 0.1 to 5% by weight, preferably from 0.5 to 2% by weight, based on the weight of the carrier. The supported catalysts can be prepared by any conventional method, for example, the method described in "Kimio Tarama, *Practical catalysts by Type of Reaction* (Tokyo: Kagaku Kogyosha Inc., Dec. 25, 1970) p. 134–137", wherein a carrier is impregnated with an aqueous solution of palladium salt and, after drying, the palladium salt is reduced in situ.

The reaction according to this invention is performed by bringing the above described catalyst into contact with the gaseous mixture comprising acetic anhydride, hydrogen and desirably acetic acid, and optionally nitrogen gas, methane gas, ethane gas and other inert diluent gases. The gaseous mixture may contain an optional proportion of acetic anhydride, the proportion being, however, generally less than about 50% and preferably 5 to 40%, in molar concentration. It is generally preferred that the molar ratio of acetic anhydride to hydrogen be in the range of from 1:20 to about 5:1.

The reaction according to the process of this invention is performed at a temperature of about 50° to 300° C., preferably from 100° to 200° C. If the reaction temperature exceeds about 300° C., methane, carbon monoxide, acetone, and other by-products are formed in an increased amount. The reaction pressure is generally desired to be within the range of from atmospheric to about 20 atm. The desired reaction can be performed under a pressure outside the range defined above, but no appreciable advantage can be obtained.

In practicing the subject invention, the catalyst layer may take any of the forms such as a fixed, a fluidized or a moving bed, though a fixed bed is advantageous because the catalyst is not worn out during the reaction. In the fixed bed, the gaseous mixture is passed over a catalyst layer comprising a catalyst supported on a carrier shaped into spherical or cylindrical particles about 3 to 6 mm in diameter at a space velocity (S.V.) of about 100 to 10,000, preferably from 300 to 5,000, liters of total gas per liter of catalyst per hour.

The following examples are given to illustrate the present invention, but they are not intended to limit the scope of the invention in any way. In the examples, all parts are by weight. The selectivities of the products other than acetic acid were calculated by the following equation:

$$\text{Selectivity for a particular product (\%)} = \frac{\text{Number of moles of a particular product produced per unit time}}{A + B \times 2 + C + D + E \times 2 + F} \times 100$$

wherein

A: the number of moles of acetaldehyde produced per unit time;

B: the number of moles of ethylidene diacetate produced per unit time;

C: the number of moles of ethyl acetate produced per unit time;

D: the number of moles of ethanol produced per unit time;

E: the number of moles of acetone produced per unit time; and

F: the number of moles of methane produced per unit time.

EXAMPLE 1

Alumina beads (diameter: 4–6 mm; "Neobead C" manufactured by Mizusawa Industrial Chemicals Ltd.) were calcined at 1000° C. for 3 hours to produce alumina having a surface area of 90 m²/g and a pore volume of 0.38 cc/g. Thirty-five parts of the alumina so prepared was added to a solution of 0.97 part of sodium palladium chloride dissolved in 50 parts of water, and the mixture was evaporated to dryness on a steam bath. The palladium salt on alumina was then reduced with hydrazine hydrate, washed with water thoroughly and dried. A hard glass reaction tube (ID=10 mm) was filled with 10 g of the resulting catalyst (ca. 10 cc) and supplied with a gas mixture (acetic anhydride to hydrogen molar ratio=20:80) at a rate of 5 liters per hour at 160° C. and under atmospheric pressure. Acetaldehyde was produced at a rate of 57 g per liter of the catalyst per hour, and about 1.1 moles of acetic acid per mole of acetaldehyde was produced. Small amounts of by-products such as ethylidene diacetate, ethyl acetate, ethanol, acetone, carbon monoxide and methane were also produced. The selectivities for the respective products were as follows:

| Acetaldehyde | 92% |
|---|---|
| Ethylidene diacetate | 3.5% |
| Ethyl acetate | 2.8% |
| Ethanol | 0.3% |
| Acetone | 0.7% |
| Carbon monoxide and methane | trace |

EXAMPLE 2

Using the same catalyst and the same apparatus as used in Example 1, the reaction tube was supplied with a gas mixture (acetic anhydride/hydrogen/nitrogen molar ratio=20:30:50) under the same reaction conditions as used in Example 1. Acetaldehyde was produced at a rate of 45 g per liter of the catalyst per hour, and about 1.05 moles of acetic acid per mole of acetaldehyde was produced. Small amounts of by-products such as ethylidene diacetate, ethyl acetate, ethanol, acetone, carbon monoxide and methane were also produced. The selectivities for the respective products were as follows:

| Acetaldehyde | 95% |
|---|---|
| Ethylidene diacetate | 1.8% |
| Ethyl acetate | 0.9% |
| Ethanol | 0.2% |
| Acetone | 1.5% |
| Carbon monoxide and methane | trace |

EXAMPLE 3

Cylindrical beads of silica 3 mm in diameter and 3–5 mm high ("N608" manufactured by Nikki Chemical Co., Ltd.) were impregnated with an aqueous solution of sodium palladium chloride in such a manner that 0.7 wt% of palladium was supported on the silica. The palladium on silica was dried at 100° C. and subsequently treated in the same manner as in Example 1 to prepare a catalyst. The same reaction tube as used in Example 1 was filled with 10 cc of the catalyst and supplied with a gas mixture (acetic anhydride/hydrogen molar ratio=30:70) at a rate of 6 liters per hour at 180° C. and under atmospheric pressure. Acetaldehyde was produced at a rate of 60 g per liter of the catalyst per hour, and the selectivity for acetaldehyde was 94%. About 1.05 moles of acetic acid was produced per mole of acetaldehyde. The selectivity for the products other than acetaldehyde and acetic acid were 0.9% for ethylidene diacetate, 1.5% for ethyl acetate, 0.3% for ethanol, and 1.8% for acetone. Only traces of carbon monoxide and methane were produced.

EXAMPLE 4

Spherical beads of titania having a surface area of 34 m²/g and a diameter of 3–4 mm ("CS-200-24" manufactured by Sakai Chemical Industries Co., Ltd.) were impregnated with an aqueous solution of sodium palladium chloride in such a manner that 0.5 wt% of palladium was supported on the titania. The palladium on titania was dried at 100° C. and subsequently treated in the same manner as in Example 1 to prepare a catalyst. The same reaction tube as used in Example 1 was filled with 10 cc of the catalyst and supplied with a gas mixture (acetic anhydride/hydrogen/nitrogen molar ratio=20:30:50) at a rate of 6 liters per hour at 190° C. and under atmospheric pressure. Acetaldehyde was produced at a rate of 55 g per liter of the catalyst per hour, and the selectivity for acetaldehyde was 91%. About 1.1 moles of acetic acid was produced per mole of acetaldehyde. Small amounts of by-products such as ethylidene diacetate, ethyl acetate, ethanol, acetone, carbon monoxide and methane were produced.

EXAMPLE 5

A pressure flow reactor having a stainless steel reaction tube (ID=16 mm) was charged with 10 cc of the same catalyst as used in Example 4. While nitrogen gas was introduced into the reactor, the reaction tube was heated to 190° C., and was then supplied with a gas mixture (acetic anhydride/hydrogen/nitrogen molar ratio=10:10:80) at a rate of 30 liters (atm. 0° C.) per hour at about 190° C. and under a pressure of 5 atm. Acetaldehyde was produced at a rate of 155 g per liter of the catalyst per hour, and its selectivity was 89%. About 1.1 moles per mole of acetaldehyde was produced. Small amounts of by-products such as ethylidene diacetate, ethyl acetate, ethanol, carbon monoxide and methane were produced.

EXAMPLE 6

Thirty-five parts of the same alumina as used in Example 1 was added to a solution of 0.57 part of tetrachloroplatinic acid ($H_2PtCl_4.6H_2O$) dissolved in 50 parts of water, and the mixture was evaporated to dryness on a steam bath. The mixture was then treated with hydrazine hydrate, whereby the platinum salt was reduced to metallic platinum. The supported platinum catalyst obtained was washed with water thoroughly and dried. The same reaction tube as used in Example 1 was filled with 10 g of the resulting catalyst (ca. 10 cc) and supplied with a gas mixture (acetic anhydride to hydrogen molar ratio=20:80) at a rate of 5 liters per hour at 180° C. and under atmospheric pressure. Acetaldehyde was produced at a rate of 25 g per liter of the catalyst per hour, and about 1.1 moles of acetic acid per mole of acetaldehyde was produced. Small amounts of by-products such as ethylidene diacetate, ethyl acetate, ethanol, acetone, carbon monoxide and methane were also produced. The selectivities for the respective products were as follows:

| | |
|---|---|
| Acetaldehyde | 95% |
| Ethyl acetate | 0.5% |
| Ethanol | 1.5% |
| Acetone | 2.8% |
| Ethylidene diacetate, carbon monoxide and methane | trace |

EXAMPLE 7

As a catalyst, use was made of a catalyst containing 0.5 wt% of platinum metal supported on an alumina pellet with a diameter of 3 mm and a height of 3.5 mm ("0.5% Pt-Alumina Pellet" produced by Nippon Engelhard Ltd.). The same reaction tube as used in Example 1 was filled with 10 g of the above catalyst and supplied with a gas mixture (acetic anhydride/hydrogen molar ratio=35:65) at a rate of 7 liters per hour at 160° C. and under atmospheric pressure. Acetaldehyde was produced at a rate of 18 g per liter of the catalyst per hour, and the selectivity for acetaldehyde was 94%. About 1.05 moles of acetic acid was produced per mole of acetaldehyde. The selectivities for the products other than acetaldehyde and acetic acid were 2.7% for ethyl acetate, 2.1% for ethanol, and 1.1% for acetone. Only traces of ethylidene diacetate, carbon monoxide and methane were produced.

EXAMPLE 8

Spherical beads of titania having a surface area of 34 $m^2/g$ and a diameter of 3-4 mm ("CS-200-24" manufactured by Sakai Chemical Industries Co., Ltd.) were impregnated with an aqueous solution of tetrachloroplatinic acid in such a manner that 1.0 wt% of platinum was supported on the titania. The platinum on titania was dried at 100° C. and subsequently treated in the same manner as in Example 1 to prepare a catalyst. The same reaction tube as used in Example 1 was filled with 10 cc of the catalyst and supplied with a gas mixture (acetic anhydride/hydrogen molar ratio=20:30:50) at a rate of 7 liters per hour at 180° C. and under atmospheric pressure. Acetaldehyde was produced at a rate of 15 g per liter of the catalyst per hour, and the selectivity for acetaldehyde was 89%. About 1.1 moles of acetic acid was produced per mole of acetaldehyde. The selectivities for the other products other than acetaldehyde and acetic acid were 3.1% for ethyl acetate, 1.9% for ethanol, and 5.0% for acetone. Only traces of ethylidene diacetate, carbon monoxide and methane were produced.

EXAMPLE 9

The same titania as used in Example 4 was impregnated with an aqueous solution of rhodium chloride in such a manner that 1.0 wt% of rhodium was supported on the titania and then dried at 100° C. The rhodium chloride on titania was oxidized at 400° C. by means of air to rhodium oxide. The resultant rhodium oxide was heated in a stream of hydrogen while increasing temperature from room temperature to 300° C. until the rhodium oxide was reduced, and further heated at 300° C. for 1 hour to prepare a catalyst. The catalyst thus obtained contained 1.0 wt% of rhodium, based on the weight of titania. The same reaction tube as used in Example 1 was filled with 10 cc of the catalyst and the reaction was conducted under the same conditions and using the same procedure as in Example 7. Acetaldehyde was produced at a rate of 8 g per liter of the catalyst per hour, and the selectivity for acetaldehyde was 82%. About 1.2 moles of acetic acid was produced per mole of acetaldehyde. Small amounts of by-products such as acetone, ethyl acetate, ethanol, ethylidene diacetate, carbon monoxide and methane were produced. The selectivity for acetone was 16%.

EXAMPLE 10

As a catalyst, use was made of a catalyst containing 0.5 wt% of rhodium metal supported on an alumina pellet with a diameter of 3 mm and a height of 3.5 mm ("0.5% Rh-Alumina Pellet" produced by Nippon Engelhard Ltd.). The same reaction tube as used in Example 1 was filled with 10 g of the above catalyst and the reaction was conducted under the same conditions and using the same procedure as in Example 8. Acetaldehyde was produced at a rate of 11 g per liter of the catalyst per hour, and the selectivity for acetaldehyde was 77%. About 1.3 moles of acetic acid was produced per mole of acetaldehyde. Small amounts of by-products such as acetone, ethyl acetate, ethanol, ethylidene diacetate, carbon monoxide and methane were produced. The selectivity for acetone was 21%.

EXAMPLE 11

The same alumina used in Example 1 was calcined at 1200° C. for 3 hours to produce alumina having a surface area of 9 $m^2/g$ and a pore volume of 0.21 cc/g. Fifty parts of the alumina so prepared was added to a solution which had 0.80 part of sodium palladium chloride dissolved in 50 parts of water, and the mixture was evaporated to dryness on a steam bath. The palladium salt on alumina was then reduced with hydrazine hydrate, washed with water thoroughly and dried. The same reaction tube as used in Example 1 was filled with 10 g of the resulting catalyst (ca. 8 cc) and supplied with a gas mixture (acetic anhydride/acetic acid/hydrogen molar ratio=30:8:62) at a rate of 12 liters per hour at 180° C. and under atmospheric pressure. After 2 hours of the reaction, the reaction mixture was analyzed. It was revealed that acetaldehyde was produced at a rate of 148 g per liter of the catalyst per hour, and about 1.15 moles of acetic acid per mole of acetaldehyde was produced. The selectivity for acetaldehyde was 90%. The selectivities for the products other than acetaldehyde and acetic acid were 2.6% for ethylidene diacetate, 3.2% for ethyl acetate, and 4.0% for methane and carbon monoxide. Only traces of acetone and ethanol were produced. Reaction was continuously carried out under the same conditions as afore-mentioned. After 30 days of the reaction, the rate of formation of acetaldehyde was 135 g per liter of the catalyst per hour, and the selectivities for the products were almost the same as the corresponding selectivites after 2 hours.

The above-mentioned procedure was followed except that a gas mixture (acetic anhydride to hydrogen molar ratio=30:70) was used. The rates of formation of acetaldehyde at 2 hours and 30 days after commencement of the reaction were 142 g and 52 g per liter of the catalyst per hour, respectively. Substantial decrease in the formation rate was found. The selectivities for acetaldehyde and other products after 2 hours and 30 days were almost the same as that obtained in Example 11.

EXAMPLE 12

Using the same catalyst as used in Example 11 and the same apparatus as used in Example 1, the reaction tube was supplied with a gas mixture (acetic anhydride/acetic acid/hydrogen molar ratio=30:25:45) under the same reaction conditions as used in Example 11. After 2 hours of the reaction, acetaldehyde was produced at a rate of 91 g per liter of the catalyst per hour, and the selectivity for acetaldehyde was 92%. About 1.1 moles of acetic acid was produced per mole of acetaldehyde. The selectivities for the products other than acetaldehyde and acetic acid were 1.8% for ethylidene diacetate, 2.8% for ethyl acetate, and 3.0% for methane and carbon monoxide. Only traces of acetone and ethanol were produced. The rate of formation of acetaldehyde and the selectivity for acetaldehyde after 40 days were almost the same as those after 2 hours.

EXAMPLE 13

Using the same catalyst and the same apparatus as used in Example 1, the reaction tube was supplied with a gas mixture (acetic anhydride/acetic acid/hydrogen molar ratio=20:6:77) at a rate of 15 liters per hour at 165° C. and under atmospheric pressure. After 2 hours of the reaction, acetaldehyde was produced at a rate of 70 g per liter of the catalyst per hour, and about 1.1 moles of acetic acid per mole of acetaldehyde was produced. The selectivity for acetaldehyde was 91%. The selectivities for the products other than acetaldehyde and acetic acid were 2.0% for ethylidene diacetate, 2.5% for ethyl acetate, and 3.5% for methane and carbon monoxide. Only traces of acetone and ethanol were produced. Reaction was continuously carried out under the same conditions as afore-mentioned. After 30 days of the reaction, the rate of formation of acetaldehyde was 68 g per liter of the catalyst per hour and the selectivities for the products were almost the same as those after 2 hours.

The above-mentioned procedure was followed except that a gas mixture (acetic anhydride to hydrogen molar ratio=20:80) was used. The rates of formation of acetaldehyde at 2 hours and 30 days after commencement of the reaction were 69 g and 28 g per liter of the catalyst per hour respectively. Substantial decrease in the formation rate was found. The selectivities for acetaldehyde and other products after 2 hours and 30 days were almost the same as that obtained in Example 13.

EXAMPLE 14

Using the same catalyst as used in Example 3 and the same apparatus as used in Example 1, the reaction tube was supplied with a gas mixture (acetic anhydride/acetic acid/hydrogen molar ratio=35:5:60) at a rate of 15 liters per hour at 170° C. and under atmospheric pressure. After 2 hours of the reaction, acetaldehyde was produced at a rate of 62 g per liter of the catalyst per hour, and about 1.05 moles of acetic acid per mole of acetaldehyde was produced. The selectivity for acetaldehyde was 92%. The selectivities for the products other than acetaldehyde and acetic acid were 1.2% for ethylidene diacetate, 1.8% for ethyl acetate, and 4.0% for methane and carbon monoxide. Only traces of acetone and ethanol were produced. Reaction was continuously carried out under the same conditions as afore-mentioned. After 20 days of the reaction, the rate of formation of acetaldehyde was 59 g per liter of the catalyst per hour, and the selectivities for the products were almost the same as those after 2 hours.

The above-mentioned procedure was followed except that a gas mixture (acetic anhydride/hydrogen molar ratio=35:65) was used. The rate of formation of acetaldehyde at 2 hours after commencement of the reaction was 60 g per liter of the catalyst per hour. After 20 days of the reaction, the rate of formation of acetaldehyde decreased to 22 g per liter of the catalyst per hour. The selectivities for acetaldehyde and other products after 2 hours and 20 days were almost the same as that obtained in Example 14.

EXAMPLE 15

Using the same catalyst as used in Example 8 and the same apparatus as used in Example 1, the reaction tube was supplied with a gas mixture (acetic anhydride/acetic acid/nitrogen molar ratio=20:3:50:28) at a rate of 12 liters per hour at 185° C. and under atmospheric pressure. After 2 hours of the reaction, acetaldehyde was produced at a rate of 22 g per liter of the catalyst per hour, and the selectivity for acetaldehyde was 87%. About 1.15 moles of acetic acid was produced per mole of acetaldehyde. The selectivities for the products other than acetaldehyde and acetic acid were 3.8% for ethylidene diacetate, 2.5% for ethyl acetate, and 6.0% for carbon monoxide and methane. Only traces of acetone and ethanol were produced. Reaction was continuously carried out under the same conditions as afore-mentioned. After 15 days of the reaction, the rate of formation of acetaldehyde was 20 g per liter of the catalyst per hour, and the selectivities for the products were almost the same as those after 2 hours.

The above-mentioned procedure was followed except that a gas mixture (acetic anhydride/hydrogen/nitrogen molar ratio=20:50:30) was used. The rate of formation of acetaldehyde at 2 hours after commencement of the reaction was 20 g per liter of the catalyst per hour. After 15 days of the reaction, the rate of formation of acetaldehyde decreased to 12 g per liter of the catalyst per hour. The selectivities for acetaldehyde and other products after 2 hours and 15 days were almost the same as that obtained in Example 15.

EXAMPLE 16

The reaction of acetic anhydride with hydrogen was carried out by the procedure and under the conditions of Example 13 except that the same catalyst as used in Example 10 was used. After 2 hours of the reaction, acetaldehyde was produced at a rate of 12 g per liter of the catalyst per hour, and the selectivity for acetaldehyde was 76%. About 1.3 moles of acetic acid per mole of acetaldehyde was produced. The selectivity for acetone was 18%. Only traces of ethyl acetate, ethylidene diacetate, carbon monoxide, methane and ethanol were produced. The rate of formation of acetaldehyde and the selectivity for acetaldehyde after 10 days were almost the same as those after 2 hours.

The above-mentioned procedure was followed except that a gas mixture (acetic anhydride/hydrogen molar ratio=20:80) was used. The rate of formation of acetaldehyde after 2 hours of the reaction was 12 g per liter of the catalyst per hour. After ten days of the reaction, the rate of formation of acetaldehyde decreased to 5 g per liter of the catalyst per hour.

What we claim is:

1. A process for producing acetaldehyde by reacting acetic anhydride with hydrogen in gaseous phase at a temperature of about 50° to 300° C. and under a pressure of atmospheric to about 20 atmospheres in the presence of palladium metal which is supported on a carrier, the concentration of palladium being in the range of from 0.1 to 5% by weight, based on the weight of the carrier.

2. A process as claimed in claim 1, wherein the gaseous mixture to be supplied to the reaction tube contains acetic acid in an amount of at least 3 mol%, based on the amount of acetic anhydride.

* * * * *